United States Patent [19]

Loftsson

[11] Patent Number: 5,324,718
[45] Date of Patent: Jun. 28, 1994

[54] CYCLODEXTRIN/DRUG COMPLEXATION

[76] Inventor: Thorsteinn Loftsson, Sorlaskjol 44, IS-101 Reykjavik, Iceland

[21] Appl. No.: 912,853

[22] Filed: Jul. 14, 1992

[51] Int. Cl.$^5$ ..................... A61K 31/735; C08B 37/16
[52] U.S. Cl. ..................... 514/58; 536/103; 514/772.2; 514/772.3; 514/772.6; 514/773; 514/777; 514/779; 514/781
[58] Field of Search ..................... 514/58, 772.2, 772.3, 514/772.6, 773, 777, 779, 781; 536/103

[56] References Cited

U.S. PATENT DOCUMENTS

| | | | |
|---|---|---|---|
| 3,459,731 | 8/1969 | Gramera et al. | 260/209 |
| 4,596,795 | 6/1986 | Pitha | 514/58 |
| 4,727,064 | 2/1988 | Pitha | 514/58 |
| 4,834,985 | 5/1989 | Elger et al. | 424/488 |
| 4,983,586 | 1/1991 | Bodor | 514/58 |
| 5,002,935 | 3/1991 | Bodor | 514/58 |
| 5,017,566 | 5/1991 | Bodor | 514/58 |
| 5,024,998 | 6/1991 | Bodor | 514/58 |
| 5,120,546 | 6/1992 | Hansen et al. | 424/448 |

FOREIGN PATENT DOCUMENTS

| | | |
|---|---|---|
| 0213514 | 3/1987 | European Pat. Off. |
| 0327766 | 8/1989 | European Pat. Off. |
| 0149197 | 3/1990 | European Pat. Off. |
| 472327 | 2/1992 | European Pat. Off. |
| 466134 | 1/1992 | Sweden |
| 91/04026 | 4/1991 | World Int. Prop. O. |
| 92/09307 | 6/1992 | World Int. Prop. O. |

OTHER PUBLICATIONS

Villiers, C. R. *Acad. Sci.*, 112, 536-538(1891).
Schardinger, *Z. Unters. Nahr. Genussm.*, 6, 865-880(1903).
Szejtli, *Pharm. Techn. Int.*, 3(2), 15-22(1991).
Szejtli, *Pharm. Techn. Int.*, 3(3), 16-24(1991).
Loftsson et al., *Pharm. Ztg. Wiss.*, 4/136:5-10(1991).
Hirayama et al., in *Cyclodextrins and their industrial uses*, ed. D. Duchêne, Editions de Santé, Paris, 1987, pp. 133-172.
Hassan et al., *Int. J. Pharm.* 58, 19-24(1990).
Nakai et al., *Chem. Pharm. Bull*, 35(11), 4609-4615(1987).
Nakai et al., *Chem. Pharm. Bull*, 37(4), 1055-1058(1989).
Nakai et al., *Chem. Pharm. Bull*, 38(3), 728-732(1990).
Nakai et al., *Chem. Pharm. Bull.*, 38(5), 1345-1348(1990).
Nakai et al., *Chem. Pharm. Bull.*, 39(6), 1532-1535(1991).
Schmidt et al., *Starch/Starke*, 39(6), 203-207(1987).
Loftsson et al., *Acta. Pharm. Nord*, 1(4), 185-193(1989).
*Remington's Pharmaceutical Sciences*, 18th edition, Alfonso R. Gennaro (ed.), Mack Publishing Co., Easton, PA, 1990, pp. 291-294.
Martin et al., *Physical Pharmacy*, 3rd edition, Lea & Febinger, Philadelphia, PA, 1983, pp. 592-638.
Florence et al., *Physicochemical Principles of Pharmacy*, 2nd edition, MacMillan Press, London, 1988, pp. 281-334.

(List continued on next page.)

*Primary Examiner*—Ronald W. Griffin
*Attorney, Agent, or Firm*—Burns, Doane, Swecker & Mathis

[57] ABSTRACT

The invention provides a method for enhancing the complexation of a cyclodextrin with a lipophilic and/or water-labile drug, comprising combining from about 0.1 to about 70% (weight/volume) of a cyclodextrin and from about 0.01 to about 5% (weight/volume) of a pharmaceutically acceptable, pharmacologically inactive, water-soluble polymer in an aqueous medium with a lipophilic and/or water-labile drug to form a drug complex, optionally followed by removal of water. Related methods, co-complexes of drug/cyclodextrin/polymer, pharmaceutical compositions and cyclodextrin/polymer complexing agents are also provided.

52 Claims, 3 Drawing Sheets

OTHER PUBLICATIONS

Leung et al., in *Controlled Drug Delivery*, 2nd edition, Robinson and Lee, editors, Marcel Dekker, Inc., New York, 1987, pp. 433–480.

Uekama et al, *Journal of Inclusion Phenomena*, 1, 309–312 (1984).

J. S. Pagington, "B–cyclodextrin; the success of molecular inclusion", *Chemistry in Britain*, May 1987, pp. 455–458.

STN Filer Supplier & File Medline AN=92324215 (Orienti et al.).

Chemical Abstracts, vol. 107, No. 16, 1987, abstract No. 140916f.

Database WPI, Week 9037, Derwent Publication Ltd., London, GB, AN 90–279330.

Loftsson et al, Eur. J. Pharm. Biopharm., vol. 37, No. 1, Mar. 1991, 30—33.

The Merck Index, eleventh edition, ed. Susan Budavari et al, Merck & Co., Inc., Rahway, N.J., 1989, pp. 959, 1248 and 1467.

Cosmetic and Drug Preservation: Principles and Practice, ed. Jon J. Kabara, Marcel Dekker, Inc., New York, N.Y., 1984, pp. 71–72.

The United States Pharmacopeia, USP XXII, twenty-second revision, Jan. 1, 1990, U.S. Pharmacopeial Convention, Inc., Rockville, Md., p. 8.

CYCLODEXTRIN/DRUG COMPLEXATION

FIELD OF THE INVENTION

The present invention relates to the use of certain polymers in the preparation of cyclodextrin-drug complexes as a means for increasing the solubilizing and stabilizing effects of cyclodextrin derivatives on drugs, and complexation therewith. Pharmaceutical compositions comprising complexes prepared according to these methods are characterized by fast and efficient drug release. The invention further relates to polymer/cyclodextrin complexing agents.

BACKGROUND OF THE INVENTION

Formulation of pharmaceutical dosage forms is frequently hampered by the poor aqueous solubility and stability of the drugs, which in turn can severely limit their therapeutic application. Also, the slow dissolution of solid state drug formulations and the side-effects of some drugs result from their poor aqueous solubility. Drug degradation products, formed in the pharmaceutical dosage forms, can also result in severe side-effects. Increasing drug solubility and stability through appropriate formulation can, thus, lead to increased therapeutic efficiency of the drug. Various methods have been used to increase the solubility and stability of drugs, such as the use of organic solvents, emulsions, liposomes and micelles, adjustments of pH and the dielectric constant of the solvent system, chemical modifications, and complexation of the drugs with appropriate complexing agents, e.g. cyclodextrins.

Cyclodextrins were first isolated by Villiers in 1891 as a digest of *Bacillus amylobacter* on potato starch [see A. Villiers: Sur la fermentation de la fécule par l'action du ferment butyriqué. *C.R. Acad. Sci.*, 112, 536–538 (1891)], but the foundations of cyclodextrin chemistry were laid down by Schardinger in the period 1903-1911 [see, for example, F. Schardinger: Über thermophile Bacterien aus verschiedenen Speisen und Milch, sowie über einige Umsetzungsproducte darselben in kohlenhydrathaltigen Nährlösungen, darunter krystallisierte Polysaccharide (Dextrine) aus Stärke, *Z. Unters. Nahr. GenuBm.*, 6, 865–880 (1903)] and much of the older literature refers to cyclodextrins as Schardinger's dextrins. Until 1970, only small amounts of cyclodextrins could be produced in the laboratory and the high production cost prevented the usage of cyclodextrins in industry. In recent years, dramatic improvements in cyclodextrin production and purification have been achieved and the cyclodextrins have become much cheaper. This has made industrial application of cyclodextrins possible.

Cyclodextrins are cyclic oligosaccharides with hydroxyl groups on the outer surface and a void cavity in the center. Their outer surface is hydrophilic, and therefore they are usually soluble in water, but the cavity has a lipophilic character. The most common cyclodextrins are α-cyclodextrin, β-cyclodextrin and γ-cyclodextrin, consisting of 6, 7 and 8 α-1,4-linked glucose units, respectively. The number of these units determines the size of the cavity.

Cyclodextrins are capable of forming inclusion complexes with a wide variety of hydrophobic molecules by taking up a whole molecule, or some part of it, into the cavity. The stability of the complex formed depends on how well the guest molecule fits into the cyclodextrin cavity. Common cyclodextrin derivatives are formed by alkylation (e.g. methyl- and ethyl-β-cyclodextrin) or hydroxyalkylation of the hydroxyl groups (e.g. hydroxypropyl- and hydroxyethyl-derivatives of α-, β-, and γ-cyclodextrin) or by substituting the primary hydroxyl groups with saccharides (e.g. glucosyl- and maltosyl-β-cyclodextrin). Hydroxypropyl-β-cyclodextrin and its preparation by propylene oxide addition to β-cyclodextrin, and hydroxyethylβ-cyclodextrin and its preparation by ethylene oxide addition to β-cyclodextrin, were described in a patent of Gramera et al. (U.S. Pat. No. 3,459,731, issued Aug. 1969) over 20 years ago. For a comprehensive review of cyclodextrins see *Cyclodextrins and their industrial uses*, editor Dominique Duchêne, Editions Santé, Paris, 1987. For a more recent overview, see J. Szejtli: Cyclodextrins in drug formulations: Part 1, *Pharm. Techn. Int.* 3(2), 15–22 (1991); and J. Szejtli: Cyclodextrins in drug formulations: Part II, *Pharm. Techn. Int.* 3(3), 16–24 (1991).

Numerous reports have been published with respect to the solubilizing effects of cyclodextrins. The general procedure described in these reports for preparing aqueous cyclodextrin solutions containing various drugs is as follows: An excess amount of the drug is added to an aqueous cyclodextrin solution and the suspension formed is agitated for up to one week at room temperature. Then the suspension is filtered or centrifuged to form a clear drug-cyclodextrin complex solution. For the preparation of solid formulations of the drug-cyclodextrin complex, the water is removed from the aqueous drug-cyclodextrin complex solution by evaporation in a rotation evaporator, in a spray dryer or by lyophilization. Pitha (Josef Pitha: Administration of sex hormones in the form of hydrophilic cyclodextrin derivatives, U.S. Pat. No. 4,596,795, issued Jun. 24, 1986) describes inclusion complexes of sex hormones, particularly testosterone, progesterone, and estradiol, with specific cyclodextrins, preferably hydroxypropyl-β-cyclodextrin and poly-β-cyclodextrin. The complexes enable the sex hormones to be successfully delivered to the systemic circulation via the sublingual or buccal route. In another patent (Josef Pitha: Pharmaceutical preparations containing cyclodextrin derivatives, U.S. Pat. No. 4,727,064, issued Feb. 23, 1988) Pitha describes formulations of a number of drugs with various cyclodextrin derivatives, mainly hydroxypropyl-β-cyclodextrin but also hydroxypropyl-γ-cyclodextrin. In a series of patents (N.S. Bodor: Improvements in redox systems for brain-targeted drug delivery, U.S. Pat. No. 5,002,935, issued Mar. 26, 1991; N.S. Bodor: Pharmaceutical formulations for parenteral use, U.S. Pat. No. 4,983,586, issued Jan. 8, 1991; N. S. Bodor: Redox systems for brain-targeted drug delivery, U.S. Pat. No. 5,017,566, issued May 21, 1991; and N. S. Bodor: Pharmaceutical formulations for parenteral use, U.S. Pat. No. 5,024,998, issued Jun. 18, 1991), Bodor describes formulations of a number of drugs with hydroxypropyl, hydroxyethyl, glucosyl, maltosyl and maltotriosyl derivatives of β- and γ-cyclodextrin. Also, Brauns and Müller (U. Brauns and B. W. W. Müller: Pharmazeutische Präparate von in Wasser schwerlöslichen oder instabilen Arznelstoffen und Verfahren zu Ihrer Herstellung, European Patent No.: 0 149 197 B1 dated Mar. 21, 1990) have described formulations of drugs with various β-cyclodextrin derivatives, mainly hydroxypropyl-β-cyclodextrin. The solubilizing and stabilizing effects of hydroxypropyl-β-cyclodextrin on drugs have been reviewed by T. Loftsson, M. E. Brewster, H. Derendorf and N. Bodor: 2-Hydroxypropyl-β-cyclodextrin: Properties and usage in pharmaceutical formulations. *Pharm. Ztg. Wiss.* 4/136: 5–10 (1991).

Methods of preparing drug-cyclodextrin complexes have been described by Hirayama and Uekama [F. Hirayama and K. Uekama: Methods of investigating and preparing inclusion compounds. In: D. Duchêene (editor), Cyclodextrins and their industrial uses. Editions de Santé, Paris, 1987, pp. 133–172]. In solution, the drug-cyclodextrin complexes are prepared by the simple method described above and the complexation evaluated by determination of stability constants by a solubility method, a kinetic method, a spectroscopic method or some other analytical method. On a laboratory scale, solid drug-cyclodextrin complexes are usually formed by lyophilization of drug-cyclodextrin complex solution, but on an industrial scale, other methods are also used such as the kneading method, spray-drying, coprecipitation, neutralization and grinding methods. In none of these methods are water-soluble pharmaceutical polymers, or other polymers in general, used for enhancing the drug-cyclodextrin complexation.

There are few samples of formation of drug-cyclodextrin complexes by heating. Thus, Hassan et al., *Int. J. Pharm.* 58, 19–24 (1990), prepared a famotidine-β-cyclodextrin complex by adding the drug to aqueous β-cyclodextrin solution, heating the mixture under reflux for 1 hour and then stirring it at room temperature for 5 days. The solution which formed was concentrated by evaporation under vacuum and the precipitate which formed was filtered and dried under vacuum at 50° C. In a series of articles, Nakai et al. describe how they make cyclodextrin inclusion complexes by heating ground mixtures of physical mixtures to 60° to 130° C. in sealed containers. See Nakai et al., *Chem. Pharm. Bull.* 35(11), 4609–4615 (1987); Nakai et al., *Chem. Pharm. Bull.* 37(4), 1055–1058 (1989); Nakai et al., *Chem. Pharm. Bull.* 38(3), 728–732 (1990); Nakai et al., *Chem. Pharm. Bull.* 38(5), 1345–1348 (1990); and Nakai et al., *Chem. Pharm. Bull.* 39(6), 1532–1535 (1991). Finally, Schmidt and Maier [E. Schmidt and H. G. Maier: Thermostabile Bindung von Aromastoffen an Stärke. Teil 2: Bindung von Menthol durch Autoklavieren, *Starch/Stärke*, 39(6), 203–207 (1987)] describe formation of thermostable binding of menthol to various types of starches, including β-cyclodextrin, by autoclaving. In none of the above mentioned articles are starches, or other polymers, used to enhance complexation of drugs by cyclodextrins.

Due to the negative enthalpy of cyclodextrin complexation, the solubility enhancement of drugs by aqueous cyclodextrin solutions is generally larger at low temperature than at high temperature [T. Loftsson and N. Bodor: Effects of 2-hydroxypropyl-β-cyclodextrin on the aqueous solubility of drugs and transdermal delivery of 17β-estradiol, *Acta Pharm. Nord.*, 1(4), 185–193 (1989)]. Also, additives such as sodium chloride, buffer salts, surfactants and organic solvents (e.g. ethanol) usually reduce the solubilizing effects of cyclodextrins.

SUMMARY AND OBJECTS OF THE INVENTION

One object of the present invention is to provide a method for enhancing the complexation of cyclodextrins with lipophilic and/or water-labile drugs.

Another object of the invention is to provide a method for increasing the solubilizing and stabilizing effects of cyclodextrins on drugs which are insoluble or sparingly soluble or unstable in water.

Another object of the invention is to provide novel co-complexes of drugs, cyclodextrins and selected polymers.

Yet another object of the invention is to provide pharmaceutical compositions comprising novel drug complexes.

Still another object of the invention is to provide a novel complexing agent for use in solubilizing and/or stabilizing a lipophilic and/or water-labile drug.

In accord with these and other objects, the present invention provides the following:

(1) A method for enhancing the complexation of a cyclodextrin with a lipophilic and/or water-labile drug, comprising combining from about 0.1 to about 70% (weight/volume) of a cyclodextrin and from about 0.01 to about 5% (weight/volume) of a pharmaceutically acceptable, pharmacologically inactive, water-soluble polymer with a lipophilic and/or water-labile drug in an aqueous medium to form a drug complex, optionally followed by removal of water;

(2) A method for solubilizing and/or stabilizing a lipophilic and/or water-labile drug in an aqueous medium, comprising complexing the drug in an aqueous medium with from about 0.1 to about 70% (weight/volume) of cyclodextrin and from about 0.01 to about 5% (weight/volume) of a pharmaceutically acceptable, pharmacologically inactive, water-soluble polymer;

(3) A co-complex of a lipophilic and/or water-labile drug with a cyclodextrin and a pharmaceutically acceptable, pharmacologically inactive, water-soluble polymer, the ratio by weight of cyclodextrin to polymer being from about 1:1 to about 5000:1, preferably from about 4:1 to about 500:1;

(4) A pharmaceutical composition comprising:

(a) a drug complex prepared by complexing, in an aqueous medium, a lipophilic and/or water-labile drug with from about 0.1 to about 70% (weight/volume) of cyclodextrin in the presence of from about 0.01 to about 5% (weight/volume) of a pharmaceutically acceptable, pharmacologically inactive, water-soluble polymer, optionally followed by removal of water; and (b) a non-toxic, pharmaceutically acceptable carrier therefor;

(5) A pharmaceutical composition comprising:

(a) a co-complex of a lipophilic and/or water-labile drug with a cyclodextrin and a pharmaceutically acceptable, pharmacologically inactive, water-soluble polymer, the ratio by weight of cyclodextrin to polymer being from about 1:1 to about 5000:1; preferably from about 4:1 to about 500:1; and (b) a non-toxic, pharmaceutically acceptable carrier therefor; and (6) A complexing agent for use in solubilizing and/or stabilizing a lipophilic and/or water-labile drug, comprising a cyclodextrin and a pharmaceutically acceptable, pharmacologically inactive, water-soluble polymer, the ratio by weight of cyclodextrin to polymer being from about 1:1 to about 5000:1, preferably from about 4:1 to about 500:1.

BRIEF DESCRIPTION OF THE DRAWINGS

Other objects and advantages of the present invention will be apparent from the following detailed description and accompanying drawings, in which.

DETAILED DESCRIPTION OF THE INVENTION AND PREFERRED EMBODIMENTS

Here and throughout this description, the following definitions are applicable:

The term "lipophilic" is used herein to describe drugs which are lipid-soluble and hydrophobic, i.e. which are insoluble or sparingly soluble in water.

The term "water-labile" is used herein to describe drugs which are unstable in water.

Cyclodextrins for use in the present invention include the natural cyclodextrins and their derivatives, including the alkylated and hydroxyalkylated derivatives and the branched cyclodextrins. Cyclodextrins and their derivatives which have been previously described as useful for complexation with drugs are of particular interest herein. In addition to α-, β- and γ-cyclodextrins, the ether and mixed ether derivatives and those derivatives bearing sugar residues are of special interest. Especially useful herein are the hydroxyethyl, hydroxypropyl (including 2- and 3-hydroxypropyl) and dihydroxypropyl ethers, their corresponding mixed ethers and further mixed ethers with methyl or ethyl groups, such as methyl-hydroxyethyl, ethyl-hydroxyethyl and ethyl-hydroxypropyl ethers of α-, β- and γ-cyclodextrin; and the maltosyl, glucosyl and maltotriosyl derivatives of β- and γ-cyclodextrin, which may contain one or more sugar residues, e.g. glucosyl or diglucosyl, maltosyl or dimaltosyl, as well as various mixtures thereof, e.g. a mixture of maltosyl and dimaltosyl derivatives. Specific cyclodextrin derivatives for use herein include hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-β-cyclodextrin, diglucosyl-β-cyclodextrin, maltosyl-β-cyclodextrin, maltosyl-γ-cyclodextrin, maltotriosyl-β-cyclodextrin, maltotriosyl-γ-cyclodextrin and dimaltosyl-β-cyclodextrin, and mixtures thereof such as maltosyl-β-cyclodextrin/dimaltosyl-β-cyclodextrin. Procedures for preparing such cyclodextrin derivatives are well-known, for example, from Bodor U.S. Pat. No. 5,024,998 dated Jun. 18, 1991, and references cited therein. Particularly preferred cyclodextrins for use in the present invention are hydroxypropyl, hydroxyethyl and dihydroxypropyl derivatives of α-, β- and γ-cyclodextrin, and their mixtures, especially those having a molar degree of substitution of from about 0.05 to about 10. The expression "molar degree of substitution" is used in the same sense as employed in Brauns and Müller European Patent No. 0149197 B1.

Suitable polymers for use herein are those which are soluble in water, are acceptable for use in pharmaceuticals and are pharmacologically inactive. Such polymers are well-known excipients commonly used in the field of pharmaceutical formulations. [See, for example, Remington's Pharmaceutical Sciences, 18th edition, Alfonso R. Gennaro (editor), Mack Publishing Company, Easton, Pa. 1990, pp. 291-294; Alfred Martin, James Swarbrick and Arthur Commarata, Physical Pharmacy. Physical Chemical Principles in Pharmaceutical Sciences, 3rd edition, Lea & Febinger, Philadelphia, Pa., 1983, pp. 592-638; A. T. Florence and D. Altwood, Physicochemical Principles of Pharmacy, 2nd edition, MacMillan Press, London, 1988, pp. 281-334.] Suitable polymers include water-soluble natural polymers, water-soluble semi-synthetic polymers (such as the water-soluble derivatives of cellulose) and water-soluble synthetic polymers. The natural polymers include polysaccharides such as inulin, pectins, algin derivatives (e.g. sodium alginate) and agar, and polypeptides such as casein and gelatin. The semi-synthetic polymers include cellulose derivatives such as methylcellulose, hydroxyethyl cellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention. Particularly preferred polymers for use herein are sodium carboxymethylcellulose, hydroxypropyl methylcellulose and polyvinylpyrrolidone.

Among the lipophilic and/or water-labile drugs which are contemplated for use in the methods and compositions of the present invention, there can be mentioned antineoplastics (anticancer/antitumor agents), sedatives, anti-inflammatory steroids (glucocorticoids), tranquilizers, anticonvulsants, antivirals, antihistaminics, vitamins/nutritional factors, emetics, anticoagulants, cardiotonics (including cardiac glycosides), diuretics, non-steroidal analgesic and/or anti-inflammatory agents (NSAID's), androgens, estrogens, anabolic agents, vasodilators, antidepressants, antipsychotics, hynotics, antifungals, progestins, antiprotozoals, anthelmintics, anesthetics, vasoconstrictors, hypoglycemics, antibacterials/antibiotics, platelat inhibitors, muscle relaxants, antiemetics, radiodiagnostics, antispasmodics, antiarrythmics, carbonic anhydrase inhibitors, gastrointestinal agents (including $H_2$-antagonists and other anti-ulcer agents), antihypertensives, serotonin antagonists, narcotic antagonists, narcotic agonists, mixed narcotic agonists-antagonists, pharmacologically active proteins such as peptide hormones, enzymes, antibodies and other biologically produced substances, anti-Parkinsonism/dopamineric agents and drugs for treating Alzheimer's disease.

It is now well-known that lipophilic and/or water-labile drugs which complex with cyclodextrin have the required shape and size to fit at least partially into the cavity of the hydrated cyclodextrin molecule; see, for example, Brauns and Müller European Patent No. 0149197 B1. Drugs whose water solubility can be improved by complexation with cyclodextrins exhibit significantly increased complexation and water solubility when treated in accord with the present invention.

Specific drugs contemplated for use in the methods and compositions of the present invention include antineoplastics such as chlorambucil, lomustine, melphalan, methotrexate, hexamethylmelamine, teniposide, etoposide, semustine (methyl CCNU), fazarabine (Ara-AC), mercaptopurine, tubulazole, carmofur, carmustine, amsacrine, doxorubicin, bruceantin, diaziquone, dideminin B, echinomycin and PCNU; anti-inflammatory steroids such as betamethasone, fludrocortisone, dexamethasone, cortisone, hydrocortisone, triamcinolone, prednisone and prednisolone; estrogens such as 17β-estradiol, 17α-ethynylestradiol (ethinylestradiol), ethynylestradiol 3-methyl ether, estrone, mestranol and estriol; progestins such as dimethisterone, norethindrone, norethindrone acetate, norgestrel, norethynodrel, ethisterone, medroxyprogesterone acetate and progesterone; anticonvulsants such as phenytoin (diphenylhydantoin) and carbamazepine; barbiturates such as pentobarbital, phenobarbital and secobarbital, variously useful as hypnotics, anticonvulsants and sedatives; antivirals such as vidarabine and virazole (also known as ribavirin); vitamins/nutritional factors such as retinol (vitamin A), vitamin A-acetate, cholecalciferol and retinal, as well as other fat-soluble vitamins such as the E, D and K vitamins; β-blockers such as timolol and atenolol, propranolol and nadolol; emetics such as apomorphine; diuretics such as chlorthalidone, furosemide and other sulfonamide-type diuretics and spironolactone, an aldosterone antagonist-type diuretic; anticoagulants such as dicumarol; cardiotonics such as digoxin and digitoxin; non-steroidal analgesics and/or anti-inflammatory agents such as aspirin, ibuprofen, indomethacin, piroxicam, sulindac and flurbiprofen; androgens such as 17-methyltestosterone and testosterone; mineral corticoids such as desoxycorticosterone; steroidal hypnotics/anesthetics such as alfaxalone; anabolic agents such as fluoxymesterone and methanstenolone; antidepressants such as sulpiride; antibiotics such as ampicillin and penicillin G; coronary vasodilators such as nitroglycerin, flunarizine, lidoflazine and mioflazine; hypnotics such as etomidate; carbonic anhydrase inhibitors such as acetazolamide, chlorzolamide, ethoxzolamine, methazolamide, L-671, 152 and MK-927; antifungals such as imidazole-type antifungals, e.g. econazole, clotrimazole, oxiconazole, bifonazole, metronidazole (metronidazole benzoate), fenticonazole, miconazole, sulconazole, tioconazole, isoconazole, butoconazole, ketoconazole, doconazole, parconazole, orconazole, valconazole and lombazole, and trizole-type antifungals, e.g. terconazole and itraconazole; antiprotozoals such as imidazole-type antiprotozoals, e.g. metronidazole, ornidazole, carnidazole, ipronidazole, tinidazole and nimorazole, and benzimidazole-type antifungals, e.g. flubendazole; H₂-antagonists, including those of the imidazole-type, e.g. burimamide, metiamide, cimetidine and oxmetidine; imidazole-type antineoplastics, such as tubulazole, a microtubule inhibitor; anthelmintic agents, including those of the benzimidazole-type, for example, thiabendazole, oxibendazole, cambendazole, fenbendazole, flubendazole, albendazole and oxfendazole; antihistaminics, including benzimidazoles such as astemizole, piperidines such as levocabastine and piperazines such as flunarizine, oxatomide and cinnarizine; antipsychotics, including those of the piperidine-type such as fluspirilene, pimozide and penfluridole; gastrointestinal agents, including piperidine derivatives such as loperamide and cisapride; serotonin antagonists, for example those of the piperidine-type such as ketanserin, ritanserin and altanserin, and those of the piperazine-type such as mianserin (also an antihistaminic); anesthetics such as lidocaine; hypoglycemics such as acetohexamide; anti-emetics such as dimenhydrinate; antibacterials such as co-trimoxazole; dopaminergic agents such as L-DOPA; anti-Alzheimer's agents such as THA; famotidine, an anti-ulcer agent/H₂-antagonist; benzodiazepines, for example chlordiazepoxide, diazepam, medazepam, oxazepam and lorazepam, variously useful as sedatives, hypnotics, anticonvulsants, tranquilizers and muscle relaxants; and prostaglandins, for example PGE's such as PGE₁ (alprostadil), a vasodilator, and PGI₂ (prostacyclin or epoprostenol), a platelet inhibitor.

In one particularly preferred aspect of the present invention, the drug contemplated for use herein is a carbonic anhydrase inhibitor, especially acetazolamide.

In another preferred aspect of the invention, the drug contemplated for use herein is a steroid, particularly an anti-inflammatory steroid (glucocorticoid), or a steroidal estrogen, progestin, anabolic agent, androgen, anesthetic/hypnotic or diuretic/aldosterone antagonist.

In yet another preferred aspect of the invention, the drug contemplated for use herein is the reduced, dihydropyridine form of a dihydropyridine ⇌ pyridinium salt redox system for brain-targeted drug delivery.

With respect to the redox system for brain-targeted drug delivery, the following definitions are applicable:

The term "lipoidal" is intended to designate a redox moiety which is lipid-soluble or lipophilic.

The terms "redox carrier system" and "redox analog system" are intended to designate two different approaches to targeting drugs to the brain using a dihydropyridine ⇌ pyridinium salt system; compounds representing either of these approaches are contemplated for use in the present invention.

The redox carrier system provides for brain-targeted drug delivery by means of carrier-drugs, which in their reduced form, which is the form intended for administration, can be represented by the formula

[D-DHC]

wherein [D] is a centrally acting drug species and [DHC] is the reduced, biooxidizable, blood-brain barrier penetrating, lipoidal form of a dihydropyridine ⇌ pyridinium salt redox carrier. In their oxidized form, which is the form "locked" in the brain from which the active drug is ultimately released, the carrier-drugs can be represented by the formula

[D-QC]⁺X⁻ wherein X⁻ is the anion of a non-toxic pharmaceutically acceptable acid, [D] is a centrally acting drug species and [QC]⁺ is the hydrophilic, ionic pyridinium salt form of a dihydropyridine ⇌ pyridinium salt redox carrier. The various redox approaches are now well-known, having been described in many patents and literature articles; the originator of the redox technology, Nicholas S. Bodor, has also described the use of cyclodextrin derivatives in conjunction with the reduced, dihydropyridine forms of the redox systems, e.g. in Bodor U.S. Pat. Nos. 4,983,586; 5,002,935; 5,017,566; and 5,024,998, all of which are incorporated by reference herein in their entirety and relied upon. While the redox systems for use herein can be any of those defined in the Bodor patents, those in which the centrally acting drug species and redox carriers are indicated in the Bodor patents as being preferred are likewise preferred for use herein. Thus, preferred redox carrier compounds of the formula [D-DHC] are those in which [D], the centrally acting drug species, is a dopaminergic agent, an androgenic agent, an anticonvulsant, an anxiolytic agent, a neurotransmitter, an antibiotic or antibacterial agent, an antidepressant, an antiviral agent, an anticancer or antitumor agent, an anti-inflammatory agent, an estrogen or a progestin, particularly when the centrally acting drug species is dopamine, testosterone, phenytoin, GABA, valproic acid, tyrosine, methicillin, oxacillin, benzylpenicilin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU. Especially preferred redox carrier compounds of the formula [D-DHC] are:

1-methyl-3-{{N-{β-[3,4-bis(pivalyloxy)phenyl]ethyl}carbamoyl}}-1,4-dihydropyridine, 1-methyl-3-{N-[[β-[3,4-bis(isobutyryloxy)phenyl]ethyl]]}carbamoyl-1,4-dihydropyridine and N-{β-[3,4-bis(pivalyloxy)phenyl]ethyl}aminocarbonyloxymethyl 1,4-dihydro-1-methyl-3-pyridinecarboxylate, which are dopamine derivatives;

17β-[(1,4-dihydro-1-methyl-3-pyridinylcarbonyl)oxy]androst-4-en-3-one and 17β-{[(3''-carbamoyl-1',4'-dihydropyridinyl)acetyl]oxy}androst-4-en-3-one, which are testosterone derivatives;

5,5-diphenyl-3-[(1'-methyl-1',4'-dihydropyridin-3'-yl)carbonyloxymethyl]-2,4-imidazolidinedione, 3-[(3'-carbamoyl-1',4'-dihydropyridin-1'-yl)acetyloxymethyl]-5,5-diphenyl-2,4-imidazolidinedione and 3-[3'-(3''-carbamoyl-1'',4''-dihydropyridin-1''-yl)propionyloxymethyl]-5,5-diphenyl-2,4-imidazolidinedione, which are phenytoin derivatives;

1-methyl-3-N-[3-(benzyloxycarbonyl)propyl]carbamoyl-1,4-dihydropyridine and 1-methyl-3-{N-[(3'-cyclohexylcarbonyl)propyl]}-carbamoyl-1,4-dihydropyridine, which are GABA derivatives;

1-methyl-3-[2'-(2''-propyl)pentanoyloxy]ethylcarbamoyl-1,4-dihydropyridine, 1-methyl-3-[2'-(2''-propyl)pentanoyloxy]ethoxycarbonyl-1,4-dihydropyridine and 1-[2'-(2''-propyl)pentanoyloxy]ethyl-3-carboxamide-1,4-dihydropyridine, which are valproic acid derivatives;

1-methyl-3-{N-[(1'-ethoxycarbonyl)-2'-(4''-pivaloyloxyphenyl)ethyl]}carbamoyl-1,4-dihydropyridine and 1-methyl-3-{N-[(1'-ethoxycarbonyl)-2'-(4''-isobutyryloxyphenyl)ethyl]}carbamoyl-1,4-dihydropyridine, which are tyrosine derivatives;

[[(1,4-dihydro-1-methyl-3-pyridinyl)carbonyl]oxy]methyl [2S-(2α,5α,6β)]-3,3-dimethyl-7-oxo-6-[(2,6-dimethoxy)benzamido]-4-thia-1-azabicyclo[3.2.0]heptane-2-carboxylate, [[(1,4-dihydro-1-methyl-3-pyridinyl)carbonyl]oxy]methyl [2S-(2α,5α,6β)-3,3-dimethyl-6-(5-methyl-3-phenyl-4-isoxazolecarboxamido-7-oxo-4-thia-1-azabicyclo[3.2.0]heptane-2-carboxylate, [[(1,4-dihydro-1-methyl-3-pyridinyl)carbonyl]oxy]methyl [2S-(2α,5α,6β)]-3,3-dimethyl-7-oxo-6-[(phenylacetyl)amino]-4-thia-1-azabicyclo[3.2.0]heptane-2-carboxylate, [[(1,4-dihydro-1-methyl-3-pyridinyl)carbonyl]oxy]methyl [2S-(2α,5α,6β)]-6-[3-(2-chlorophenyl)-5-methyl-4-isoxazolecarboxamido]-3,3-dimethyl-7-oxo-4-thia-1-azabicyclo[3.2.0]heptane-2-carboxylate and [[(1,4-dihydro-1-methyl-3-pyridinyl)carbonyl]oxy]methyl [2S-(2α,5α,6β)]-6-[3-(2,6-dichlorophenyl)-5-methyl-4-isoxazolecarboxamido]-3,3-dimethyl-7-oxo-4-thia-1-azabicyclo[3.2.0]heptane-2-carboxylate, which are derivatives of methicillin, oxacillin, benzylpenicillin, cloxacillin and dicloxacillin, respectively;

[{N-[3-(10,11-dihydro-5H-dibenz(b,f]azepin-5-yl)]propyl-N-methylamino}carbonyloxy]methyl 1,4-dihydro-1-methyl-3-pyridinecarboxylate and [1-{N-[3-(10,11-dihydro-5H-dibenz[b,f]azepin-5-yl)]propyl-N-methyl-amino}carbonyloxy]ethyl 1,4-dihydro-1-methyl-3-pyridinecarboxylate, which are derivatives of desipramine;

1-methyl-3-{[2-(9-guanylmethoxy)ethoxy]carbonyl}-1,4-dihydropyridine, which is a derivative of acyclovir;

3'-(1,4-dihydro-1-methyl-3-pyridinylcarbonyl)-5'-pivaloyltrifluorothymidine, which is a derivative of trifluorothymidine;

3'-azido-3'-deoxy-5'-(1-methyl-1,4-dihydro-3-pyridinyl)carbonyl]thymidine, which is a derivative of zidovudine (AZT);

N-(2-chloroethyl)-N'-[4-(1,4-dihydro-1-methyl-3-pyridinecarbonyloxy)cyclohexyl]-N-nitrosourea, N-(2-fluoroethyl)-N'-[2-(1,4-dihydro-1-methyl-3-pyridinecarbonyloxy)ethyl]-N-nitrosourea and N-(2-chloroethyl)-N'-[2-(1,4-dihydro-1-methyl-3-pyridinecarbonyloxy)ethyl]-N-nitrosourea, which are derivatives of hydroxy-CCNU, FENU and HENU, respectively;

1-methyl-3-[(N-{2-[4-({4-[bis(2-chloroethyl)]amino}phenyl)butanoyloxy]ethyl})carbamoyl]-1,4-dihydropyridine, 1-methyl-3-(N-{4-[4-(4-{[bis(2-chloroethyl)]amino}phenyl)butanoyloxy]cyclohexyl}carbamoyl)-1,4-dihydropyridine, 1-methyl-3-[(N-{2-[4-({4-bis(2-chloroethyl)]amino}phenyl)butanoyloxy]propyl})carbamoyl]-1,4-dihydropyridine, 1-methyl-3-[(N-{2-phenyl-2-({4-[bis(2-chloroethyl)]amino}phenyl)butanoyloxy]ethyl)carbamoyl]-1,4-dihydropyridine and 1-methyl-3-[N-({1-[4(4-{[bis(2-chloroethyl)]amino}phenyl)butanoyloxy]cyclohexyl}methyl)carbamoyl]-1,4-dihydropyridine, which are derivatives of chlorambucil;

1-methyl-3-N-[2-(3-indolyl)ethyl]carbamoyl-1,4-dihydropyridine, which is a derivative of tryptamine;

9-fluoro-11β,17-dihydroxy-16α-methyl-21-{[(1-methyl-1,4-dihydropyridin-3-yl)carbonyl]oxy}pregna-1,4-diene-3,20-dione and 11β,17-dihydroxy-21-{[(1-methyl-1,4-dihydropyridin-3-yl)carbonyl]oxy}pregn-4-ene-3,20-dione, which are derivatives of dexamethasone and hydrocortisone, respectively;

3-hydroxy-17β-[(1-methyl-1,4-dihydropyridin-3-yl)carbonyl]oxyestra-1,3,5(10)-triene, which is an estradiol derivative;

3-hydroxy-17β-{[1-methyl-1,4-dihydropyridin-3-yl)carbonyl]oxy}-19-nor-17α-pregna-1,3,5(10)-trien-20-yne, 3-[(1-methyl-1,4-dihydro-3-pyridinyl)carbonyloxy]estra-1,3,5(10)-trien-17-one, 17β-[(1-methyl-1,4-dihydro-3-pyridinyl)carbonyloxy]estra-1,3,5(10)-trien-3-ol 3-methyl ether, 3,17β-bis-{[(1-methyl-1,4-dihydropyridin-3-yl)carbonyl]oxy}estra-1,3,5(10)-triene, 3-(phenylcarbonyloxy)-17β-{[(1-methyl-1,4-dihydropyridin-3-yl)carbonyl]oxy}estra-1,3,5(10)-triene and 3-methoxy-17β-{[1-methyl-1,4-dihydropyridin-3-yl)carbonyl]oxy}-19-nor-17α-pregna-1,3,5(10)-trien-20-yne, which are derivatives of ethinyl estradiol, estrone, estradiol 3-methyl ether, estradiol, estradiol benzoate and mestranol, respectively;

17β-{[(1-methyl-1,4-dihydropyridin-3-yl)carbonyl]oxy}-19-norpregn-4-en-20-yn-3-one, 17β-{[(1-methyl-1,4-dihydropyridin-3-yl)carbonyl]oxy}pregn-4-en-20-yn-3-one, 13-ethyl-17β-{[(1-methyl-1,4-dihydropyridin-3-yl)carbonyl]oxy}-18,19-dinorpregn-4-en-20-yn-3-one and 17β-{[(1-methyl-1,4-dihydropyridin-3-yl)carbonyl]oxy}-19-norpregn-5(10)-en-20-yn-3-one, which are derivatives of norethindrone, ethisterone, norgestrel and norethynodrel, respectively;

1-methyl-3-[N-(2-{1-(p-chlorobenzoyl)-5-methoxy-2-methyl-3-indolyl]acetoxy}ethyl)carbamoyl]-1,4-dihydropyridine and 1-methyl-3-{N-[2-(6-methoxy-α-methyl-2-naphthalenylacetoxy)ethyl]carbamoyl-1,4-dihydropyridine, which are derivatives of indomethacin and naproxen, respectively; and 3-(1,4-dihydro-1-methyl-3-pyridinylcarbonyloxymethyl)-5-fluorouracil and 1-(1,4-dihydro-1-methyl-3-pyridinecarbonyloxymethyl-5-fluorouracil, which are derivatives of 5-FU (5-fluorouracil).

Quite surprisingly, it has now been found that is possible to increase the effects of cyclodextrin complexation by adding small amounts of watersoluble, pharmaceutically acceptable, pharmacologically inactive polymers to aqueous cyclodextrin/drug solutions and then preferably heating the solutions for some time. Typically, the polymer is dissolved in an aqueous solution of the cyclodextrin, or both polymer and cyclodextrin are dissolved in water, and then the drug is added. The cyclodextrin concentration can range from about 0.1 to 70% w/v and the polymer concentration from about 0.01 to about 5% w/v in the original solution. The polymer: cyclodextrin weight ratio can range from about 1:1 to about 1:5000, but is usually from about 1:4 to about 1:500, that is, 1 part of polymer to 4 to 500 parts of cyclodextrin. Since maximum complexation is ordinarily desired, the drug is usually added in excess. The drug may be dissolved in the cyclodextrin/polymer solution either before or after the cyclodextrin solution has been kept at from about 30° to about 150° C. for from about 0.1 to about 100 hours. Optionally, the polymer and cyclodextrin can be combined in aqueous solution, preferably with heating at the temperature and for the time indicated in the preceding sentence and dried (preferably lyophilized) to give a cyclodextrin/polymer combination complexing agent. That complexing agent can subsequently be combined in aqueous solution with the drug, again with or without heating for the time and at the temperature indicated above. Whatever the manner of preparing the drug/cyclodextrin/polymer aqueous solution, said solution can optionally be dried in accord with methods which are known per se. Depending on the drug employed, acid or base may be added to the cyclodextrin/polymer/drug solution during preparation.

Aqueous solutions of cyclodextrins and polymers prepared in accord with the present invention have a greater solubilizing and stabilizing effect on lipophilic and/or water-labile drugs than cyclodextrin solutions made by simply dissolving cyclodextrins in water or aqueous buffer solutions. The water-soluble pharmaceutical polymers increase the solubilizing effect of the cyclodextrins and, thus, make it possible to reduce the amount of cyclodextrin which will be present in the pharmaceutical composition ultimately administered. Aqueous cyclodextrin drug formulations containing water-soluble pharmaceutical polymers are characterized by fast and efficient drug release, which can result in a more rapid onset of the desired therapeutic response and better total bioavailability of the drugs. Solid pharmaceutical preparations, made, for example, by removal of water from the above-mentioned aqueous cyclodextrin-polymer-drug solutions, for example by lyophilization, are characterized by faster and more efficient dissolution of drugs compared to the dissolution of drugs from solid cyclodextrin preparations without polymers. This can lead to hastening the onset of the therapeutic response and can also increase the total bioavailability of drugs from solid pharmaceutical preparations.

It appears that the water-soluble polymers used in accord with the present invention after the hydration of the cyclodextrin molecules and thus their three-dimensional structure in aqueous solutions. Heating accelerates this process. It also appears that the polymer participates directly in the drug complex formation, acting as a co-complexing agent with the cyclodextrin. S. H. S. Leung, J. R. Robinson and V. H. L. Lee ["Parenteral Products", Chapter 10 in *Controlled Drug Delivery. Fundamentals and Applications*, second edition, J. R. Robinson and V. H. L. Lee, editors, Marcel Dekker, Inc., New York, 1987, pp. 433–480], in a review of studies from the 1950's and early 1960's, point out that the role of plasma protein and tissue binding in prolonging drug action is well-known, and that the same result can be achieved by forming a dissociable complex of a drug with macromolecules such as methylcellulose, carboxymethylcellulose and polyvinylpyrrolidone. Table 1 and Table 6 hereinbelow show that aqueous polymer solutions ($S_2$) solubilize drugs to a greater extent than pure water ($S_1$). This can be attributed to complexation of the drug with the polymer. Thus, the polymers and the cyclodextrins both form soluble complexes with various drug molecules and can be used to increase the aqueous solubility of the drugs. However, when polymer and cyclodextrin are mixed together in accord with the present invention, one obtains greater drug solubility enhancement than when the polymer and cyclodextrin are used separately; indeed, the combination effect is more than simply additive, it is synergistic. This is indicative of the formation of a new type of complex between the drug and the polymer-cyclodextrin. The cyclodextrin can thus be considered to be the complexing agent, the polymer a co-complexing agent, and the drug complex not simply a drug/cyclodextrin complex, but a drug/cyclodextrin/polymer co-complex.

Pharmaceutical compositions utilizing the drug/cyclodextrin/polymer products prepared in accord with the present invention can be used to treat a variety of conditions, depending upon the pharmacological nature of the drug selected for administration. The compositions contain a pharmacologically/therapeutically effective amount of the selected drug and the amounts/ratios of selected cyclodextrin and selected polymer noted hereinabove. For example, if the selected drug is an anti-inflammatory agent, a pharmacologically effective amount thereof will be an amount sufficient to elicit an anti-inflammatory response. Selection of the cyclodextrin and the polymer in the compositions will depend upon the nature of the drug and the contemplated route of administration. Virtually any route of administration by which a selected drug can be used can be employed for the instant compositions, including but not limited to parenteral, oral and topical (including ophthalmic) routes. Polymers and cyclodextrins as defined herein will be selected according to the contemplated route of administration, since some may be acceptable for certain routes of administration and not for others. For example, a hydroxyalkylated cyclodextrin such as hydroxypropyl-β-cyclodextrin rather than an alkylated cyclodextrin would be selected for intravenous use because of toxicity considerations. Similarly, only some of the polymers disclosed herein may be suitable for intravenous use, as is indeed well-known in the art.

In the case of parenteral formulations, intended, for example, for intramuscular, subcutaneous, intra-articular or intravenous administration, the pharmaceutical composition of drug/cyclodextrin/polymer will be in the form of an aqueous solution which is acceptable for parenteral administration, i.e. which is sterile and pyrogen-free and has been prepared in accord with accepted pharmaceutical procedures, for example as described in *Remington's Pharmaceutical Sciences*, seventeenth edition, ed. Alfonso R. Gennaro, Mack Publishing Company, Easton, PA (1985), pp. 1518–1552. The aqueous sterile injection solutions may further contain anti-oxidants, buffers, bacteriostats, isotonicity adjusters and like additions acceptable for parenteral formulations. Various unit dose and multidose containers, e.g. sealed ampules and vials, may be used, as is well-known in the art. The essential ingredients of the sterile parenteral formulation, i.e. the drug(s), water and selected cyclodextrin(s) and polymer(s) may be presented in a variety of ways, just so long as the solution ultimately administered to the patient contains the appropriate amounts of the essential ingredients. Thus, for example, the drug/cyclodextrin/polymer/water formulation may be presented in a unit dose or multidose container, ready for injection. As another example, a concentrated solution of drug/cyclodextrin/polymer/water may be presented in a separate container from a diluting liquid (water or cyclodextrin/water) designed so that the contents can be combined to give a formulation containing appropriate amounts for injection. As another alternative, the drug or a drug/cyclodextrin/polymer combination may be provided in a freeze-dried condition in one container, while a separate container contains diluting liquid (water or cyclodextrin/water, depending on the amount of cyclodextrin in the other container), again designed so that the contents can be combined to give a formulation containing the appropriate amounts of the essential ingredients. As yet another alternative, the cyclodextrin/polymer may be provided in a freeze-dried condition in one container, the drug in another and the diluting liquid in yet another container. In any event, the contents of each container will be sterile.

For oral administration, the pharmaceutical compositions may be in the form of any well-known oral dosage form, e.g. tablets, caplets, capsules, pills, powders, solutions, gels and the like. Orally acceptable carrier materials, including excipients, binders and disintegrators, are well-known in the art. Moreover, the usual buffers, coloring agents, flavoring agents and sweetening agents can be added, if necessary or if desired. Tablets and caplets may also be coated with the usual coating materials.

In addition to oral dosage forms which are intended to be swallowed, the present invention contemplates oral dosage forms which are intended for usage only in the oral cavity, typically mouthwashes, and those which are intended for buccal and/or sublingual administration (such as lozenges).

For rectal or vaginal administration, suppositories may be suitable, appropriate carriers for which are well-known. Similarly, for topical use, well-known topically acceptable carriers/vehicles can be employed to form creams, gels, ointments and the like. Appropriate carriers for use in nasal dosage forms (solutions, gels, ointments and the like) are similarly well-known.

In the case of ophthalmic compositions, the carrier must be a non-toxic, ophthalmically acceptable carrier. Suitable ophthalmic carriers will be apparent to those skilled in the art of ophthalmic formulations. Obviously, the choice of suitable carriers will depend on the exact nature of the particular dosage form desired, e.g. whether the drug/cyclodextrin/polymer complex is to be formulated into an ophthalmic solution or suspension (typically for use as eye drops), an ophthalmic ointment or cream or an ophthalmic gel. Preferred dosage forms are solutions, which contain a major amount of water in addition to the active ingredient. Minor amounts of other ingredients such as pH adjusters (e.g. a base such as NaOH), emulsifiers or dispersing agents, buffering agents, preservatives, wetting agents and jelling agents may also be present. Most preferably, the ophthalmic composition is a sterile, isotonic, buffered aqueous solution.

Generally speaking, the therapeutic dosage ranges for administration of drugs in the pharmaceutical formulations described herein will be the same as or less than (in some instances, substantially less than) those characteristically used for administration of the drug per se (or, in the case of the carrier-drugs, of the parent drug species per se). Naturally, such therapeutic dosage ranges will vary with the size and species of the patient, the condition for which the formulation is administered, the route of administration employed and the like. The quantity of given dosage form needed to deliver the desired dose of active ingredients will of course depend upon the concentration of the drug in the pharmaceutical formulation.

In order to further illustrate the present invention and the advantages thereof, the following specific examples are given, it being understood that same are intended only as illustrative and in no way limitative of the invention.

EXAMPLE 1

Solubilities (S) of various drugs in four different solvents, i.e. (a) water ($S_1$), (b) aqueous 0.25% (w/v) sodium carboxymethylcellulose solution (CMC) ($S_2$), (c) aqueous solution of 10% (w/v) 2-hydroxypropyl-β-cyclodextrin (HPβCD) of molar substitution (MS)=0.6 ($S_3$) and (d) aqueous solution containing both 0.25% (w/v) CMC and 10% (w/v) HPβCD MS=0.6 ($S_4$) were determined by adding an excess amount of the drug to be tested to the solvents and heating the suspensions formed in sealed containers to 120° C. The suspensions were kept at this temperature for 20 minutes and then allowed to equilibrate for 3 days at room temperature (approximately 23° C.). After equilibration, aliquots were filtered through 0.45 μm membrane filters, diluted with a mixture of methanol and water (7:3 v/v) and analyzed by an high pressure liquid chromatographic (HPLC) method. The results set forth in Table 1 show that the solubilizing effect of HPβCD was increased by 4 to 57% ($S_4/S_3$=1.04 to 1.57) when 0.25% CMC was present in the solution.

TABLE 1

The effect of CMC on the solubilization of various drugs in aqueous HPβCD solutions.

| Drug | $S_1$ (mg/ml) | $S_2$ (mg/ml) | $S_3$ (mg/ml) | $S_4$ (mg/ml) | $S_4/S_3$ |
|---|---|---|---|---|---|
| Acetazolamide | 0.70 | 0.84 | 2.52 | 3.11 | 1.23 |
| Alprazolam | 0.07 | 0.18 | 1.28 | 1.55 | 1.21 |
| Carbamazepine | 0.11 | 0.20 | 7.00 | 9.20 | 1.31 |
| Clotrimazole | 0.00 | 0.00 | 1.20 | 1.40 | 1.17 |
| Dexamethasone | 0.26 | 0.33 | 8.43 | 8.75 | 1.04 |
| Diazepam | 0.69 | 0.81 | 9.14 | 9.70 | 1.06 |
| Econazole | 0.57 | 0.60 | 4.86 | 7.41 | 1.52 |
| 17β-Estradiol | 0.01 | 0.17 | 5.10 | 5.35 | 1.05 |
| Ethoxyzolamide | 0.04 | 0.07 | 1.19 | 1.66 | 1.39 |
| Hydrocortisone | 0.36 | 1.10 | 12.88 | 17.02 | 1.32 |
| Miconazole | 0.04 | 0.06 | 1.98 | 2.50 | 1.26 |
| Oxazepam | 0.03 | 0.04 | 0.90 | 1.42 | 1.57 |
| Prednisolone | 0.38 | 0.53 | 13.60 | 15.30 | 1.13 |
| Progesterone | 0.00 | 0.00 | 4.03 | 6.11 | 1.52 |
| Sulfamethoxazole | 0.36 | 0.69 | 10.01 | 12.60 | 1.26 |
| Termazepam | 0.60 | 0.65 | 3.01 | 3.48 | 1.16 |
| Triamcinolone acetonide | 0.03 | 0.07 | 2.09 | 2.58 | 1.23 |

EXAMPLE 2

The effect of increasing CMC concentration on the solubility of three drugs in aqueous 10% (w/v) HPβCD MS=0.9 solution was also determined under the same condition as in Example 1. The results are shown in Table 2.

TABLE 2

The effect of increasing CMC concentration on solubilization.

| Drug | 0.00% CMC (w/v) | 0.10% CMC (w/v) | 0.25% CMC (w/v) | 0.50% CMC (w/v) |
|---|---|---|---|---|
| Acetazolamide | 2.52 | 3.60 | 3.21 | 3.75 |
| Hydrocortsone | 12.88 | 15.97 | 15.78 | 18.70 |
| Oxazepam | 0.90 | 1.49 | 1.31 | 1.88 |

EXAMPLE 3

The effect of heating on the solubilization of hydrocortisone in aqueous solution containing 10% (w/v) HPβCD MS=0.6 and 0.25% (w/v) CMC was investigated as follows: An excess amount of hydrocortisone was added to the solution and the suspension which was formed was heated to 120° C. in a sealed container. The suspension was kept at this temperature for (a) 20, (b) 40, (c) 60 and (d) 80 minutes. At each time point, an aliquot of the suspension was removed and allowed to equilibrate for 3 days at room temperature (approximately 23° C.). After equilibration, each aliquot was filtered through a 0.45 μm membrane filter, diluted with a mixture of methanol and water (7:3 v/v) and analyzed by HPLC. The results in Table 3 show that the solubilizing effect of the HPβCD-CMC mixture increases with increasing duration of heating.

TABLE 3

The effect of heating on the solubilization of hydrocortisone. The solubility of hydrocortisone in aqueous 10% (w/v) HPβCD-0.25% (w/v) CMC solution at room temperature.

| | Duration of heating (minutes) | | | |
|---|---|---|---|---|
| | 20 | 40 | 60 | 80 |
| Solubility (mg/ml) | 17.02 | 17.02 | 19.86 | 25.92 |

EXAMPLE 4

Figure 1:
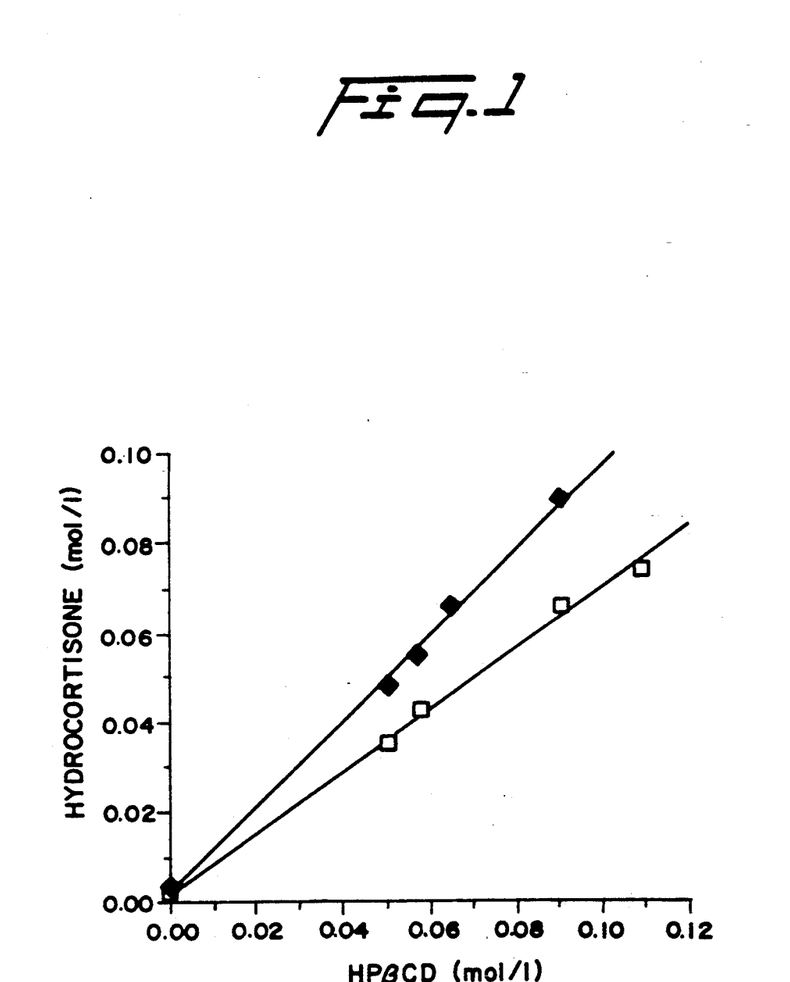
FIG. 1 is a pair of phase-solubility diagrams for hydrocortisone in aqueous HPβCD (2-hydroxypropyl-β- cyclodextrin) solutions at room temperature (23° C.), ◆ when 0.25% (w/v) CMC (sodium carboxymethylcellulose) is present in the aqueous solutions and □ when no CMC is present.

The phase-solubility diagram of hydrocortisone in aqueous HPβCD solutions with or without 0.25% (w/v) CMC was determined at room temperature. An excess amount of the drug was added to water, or aqueous 0.25% (w/v) CMC solutions, containing various amounts of HPβCD. The suspensions which formed were heated in sealed containers to 120° C. and kept at that temperature for 20 minutes. After equilibration for three days at room temperature, aliquots were removed from the containers and each aliquot was filtered through a 0.45 μm membrane filter, diluted with a mixture of methanol and water (7:3 v/v) and analyzed by HPLC. The apparent stability constant ($K_c$) for the hydrocortisone-HPβCD complex was determined by Eq. 1 from the slope of the phase-solubility diagrams (FIG. 1), assuming a 1:1 stoichiometric ratio.

$$K_c = \frac{\text{Slope}}{S_o(1 - \text{Slope})} \qquad \text{Eq. 1}$$

(In Eq. 1, $S_o$ is the solubility of the free, uncomplexed form of hydrocortisone.) The apparent stability constant was determined to be 997 liter/mole when no CMC was present in the aqueous solution but 10,043 liter/mole when 0.25% CMC was present, a tenfold increase.

EXAMPLE 5

Solubilities (S) of three drugs in four different solvents, i.e. (a) water ($S_1$), (b) aqueous 0.25% (w/v) sodium carboxymethylcellulose solution (CMC) ($S_2$), (c) aqueous solution of 10% (w/v) hydroxyethyl-β-cyclodextrin (HEβCD) of molar substitution (MS)=0.6 ($S_3$), and (d) aqueous solution containing both 0.25% (w/v) CMC and 10% (w/v) HEβCD MS=0.6 ($S_4$), were determined as in Example 1. The results in Table 4 show that the solubilizing effect of HEβCD was increased by 32 to 53% ($S_4/S_3$=1.32 to 1.53) when 0.25% (w/v) CMC was present in the solution.

TABLE 4

The effect of CMC on the solubilization of drugs in aqueous HEβCD solutions.

| Drug | $S_1$ (mg/ml) | $S_2$ (mg/ml) | $S_3$ (mg/ml) | $S_4$ (mg/ml) | $S_4/S_3$ |
|---|---|---|---|---|---|
| Hydrocortisone | 0.36 | 1.10 | 17.51 | 26.81 | 1.53 |
| Miconazole | 0.04 | 0.06 | 2.51 | 3.31 | 1.32 |
| Sulfamethoxazole | 0.36 | 0.69 | 7.07 | 9.81 | 1.39 |

EXAMPLE 6

Solubilities (S) of hydrocortisone in four different solvents, i.e. (a) water ($S_1$), (b) aqueous 0.25% (w/v) hydroxypropyl methylcellulose solution (HPMC) ($S_2$), (c) aqueous solution of 5% (w/v) 2-hydroxypropyl-α-, β-, or γ-cyclodextrin (HPαCD, HPβCD, or HPγCD) of molar substitution (MS)=0.6, 0.9 and 0.6, respectively, ($S_3$), and (d) aqueous solution containing both 0.25% (w/v) HPMC and 5% (w/v) HPαCD, HPβCD, or HPγCD ($S_4$), were determined as in Example 1. The results in Table 5 show that the solubilizing effect of the cyclodextrin derivative was increased by 10 to 50% ($S_4/S_3=1.1$ to 1.5) when 0.25% HPMC was present in the solution.

TABLE 5

The effect of HPMC on the solubilization of hydrocortisone in aqueous cyclodextrin solutions.

| Cyclodextrin | $S_1$ (mg/ml) | $S_2$ (mg/ml) | $S_3$ (mg/ml) | $S_4$ (mg/ml) | $S_4/S_3$ |
|---|---|---|---|---|---|
| HPαCD MS = 0.6 | 0.4 | 1.4 | 2.4 | 3.6 | 1.5 |
| HPβCD MS = 0.9 | 0.4 | 1.4 | 6.7 | 7.7 | 1.2 |
| HPγCD MS = 0.6 | 0.4 | 1.4 | 7.7 | 8.7 | 1.1 |

EXAMPLE 7

Solubilities (S) of three drugs in four different solvents, i.e. (a) water ($S_1$), (b) aqueous 0.25% (w/v) polyvinylpyrrolidone solution (PVP) ($S_2$), (c) aqueous solution of 10% (w/v) hydroxypropyl-β-cyclodextrin (HPβCD) of molar substitution (MS)=0.7 ($S_3$), and (d) aqueous solution containing both 0.25% (w/v) PVP and 10% (w/v) HPβCD MS=0.7 ($S_4$), were determined as in Example 1. The results in Table 6 show that the solubilizing effect of HPβCD was increased by 27 to 129% ($S_4/S_3=1.27$ to 2.29) when 0.25% (w/v) PVP was present in the solution.

TABLE 6

The effect of PVP on the solubilization of drugs in aqueous HPβCD solutions.

| Drug | $S_1$ (mg/ml) | $S_2$ (mg/ml) | $S_3$ (mg/ml) | $S_4$ (mg/ml) | $S_4/S_3$ |
|---|---|---|---|---|---|
| Acetazolamide | 0.70 | 1.05 | 2.80 | 3.66 | 1.31 |
| Carbamazepine | 0.11 | 0.31 | 6.43 | 7.50 | 1.17 |
| Clotrimazole | 0.00 | 0.00 | 1.20 | 1.80 | 1.50 |
| Dexamethasone | 0.26 | 0.33 | 7.53 | 8.00 | 1.06 |
| Econazole | 0.57 | 0.64 | 5.22 | 5.65 | 1.08 |
| 17β-Estradiol | 0.01 | — | 5.10 | 9.50 | 1.86 |
| Ethoxyzolamide | 0.04 | 0.06 | 1.36 | 2.72 | 2.00 |
| Miconazole | 0.04 | 0.20 | 2.36 | 3.40 | 1.44 |
| Progesterone | 0.00 | 0.00 | 4.76 | 5.71 | 1.20 |
| Oxazepam | 0.03 | 0.04 | 0.90 | 1.14 | 1.27 |
| Trimethoprim | 0.82 | 1.35 | 2.83 | 6.47 | 2.29 |
| Sulfamethoxazole | 0.36 | 0.86 | 5.71 | 8.92 | 1.56 |

EXAMPLE 8

Solubilities (S) of various drugs in eight different solvents, i.e. (a) water ($S_1$), (b) aqueous 10% (v/v) ethanol solution ($S_2$), (c) aqueous 0.25% (w/v) sodium carboxymethyl-cellulose solution (CMC) ($S_3$), (d) aqueous solution containing both 10% (v/v) ethanol and 0.25% (w/v) CMC ($S_4$), (e) aqueous solution of 10% (w/v) 2-hydroxypropyl-β-cyclodextrin (HPβCD) of molar substitution (MS)=0.6 ($S_5$), (f) aqueous solution containing both 10% (v/v) ethanol and 10% (w/v) HPβCD MS=0.6 ($S_6$), (g) aqueous solution containing both 0.25% (w/v) CMC and 10% (w/v) HPβCD MS=0.6 ($S_7$), and (h) aqueous solution containing 10% (v/v) ethanol, 0.25% (w/v) CMC and 10% (w/v) HPβCD MS=0.6 ($S_8$) were determined as in Example 1. The results in Table 7 show that CMC is also able to increase the solubilizing effect of HPβCD in aqueous ethanolic solutions.

TABLE 7

The effect of ethanol and CMC on the solubilizing effect HPβCD in aqueous solutions.

| | Solubility (mg/ml) | | | | | | | |
|---|---|---|---|---|---|---|---|---|
| Drug | $S_1$ | $S_2$ | $S_3$ | $S_4$ | $S_5$ | $S_6$ | $S_7$ | $S_8$ |
| Acetazolamide | 0.70 | 1.11 | 0.84 | 0.75 | 2.52 | 2.19 | 3.11 | 2.50 |
| Hydrocortisone | 0.36 | 0.83 | 1.10 | 1.53 | 12.88 | 10.91 | 20.64 | 13.27 |
| Miconazole | 0.04 | 0.31 | 0.06 | — | 1.98 | 2.22 | 2.50 | 12.55 |

EXAMPLE 9

The permeability through a semi-permeable membrane was investigated. Semipermeable cellophane membrane was placed in a Franz diffusion cell containing 10 ml aqueous 5% (w/v) HPβCD solution as the receptor phase. The donor phase consisted of a suspension of approximately 3% (w/v) hydrocortisone in (a) aqueous 10% (w/v) hydroxypropyl-β-cyclodextrin (HPβCD) solution and (b) aqueous solution containing both 10% (w/v) HPβCD and 0.25% (w/v) carboxymethyl-cellulose (CMC), and 2 ml of the donor phase applied to the membrane surface (area 3.1 cm$^2$). The assembled diffusion cells were kept at room temperature ($22°\pm1°$ C.) and samples (30 μl) were removed from the donor phase every 10 minutes, up to 2 hours, and analyzed immediately by HPLC. The results shown in Table 8 clearly indicate that hydrocortisone is released faster from a suspension containing CMC than from suspension containing no CMC.

TABLE 8

The solubility (S) and the flux (F) of hydrocortisone through a semi-permeable cellophane membrane from hydrocortisone suspensions in HPβCD vehicles.

| Vehicle composition | S (mg/ml) | F (μg/cm$^2$/minute) |
|---|---|---|
| Aqueous 10% (w/v) HPβCD solution | 14.96 | 3.02 |
| Aqueous solution containing 10% (w/v) HPβCD and 0.25% (w/v) CMC | 19.23 | 5.36 |

EXAMPLE 10

The effect of carboxymethylcellulose (CMC) on the release of hydrocortisone from tablets containing hydrocortisone HPβCD complex was investigated.

The freeze-dried hydrocortisone-HPβCD complex was prepared by adding an excess of hydrocortisone to aqueous solution containing 50% (w/w) (about 58% w/v) HPβCD and 0, 0.1 or 0.25% (w/v) CMC and heating the hydrocortisone suspensions formed for 20 minutes at 120° C. After equilibration for 3 days at room temperature, the suspensions were filtered through 0.45 μm membrane filters, the filtrates were lyophilized and the solid which formed was ground with a mortar and pestle. The amount of hydrocortisone incorporated into the HPβCD complex was determined by HPLC.

Individual disks of 200 mg hydrocortisone-HPβCD complex were compressed in a hydraulic press under vacuum and a force of $1 \times 10^4$ kg for 1.5 minutes using a 13 mm (diameter) IR potassium bromide pellet punch. The disks had a cross-sectional area of 1.33 cm$^2$. Each disk contained approximately 27 mg of hydrocortisone.

The dissolution studies were carried out a USP XXII described paddle apparatus for dissolution rate determination. The release rate was determined at 37°±1° C. and 100 rpm by adding one tablet to 900 ml of water. Samples were withdrawn at various time intervals, filtered through 0.45 membrane filters and analyzed by HPLC.

Figure 2:
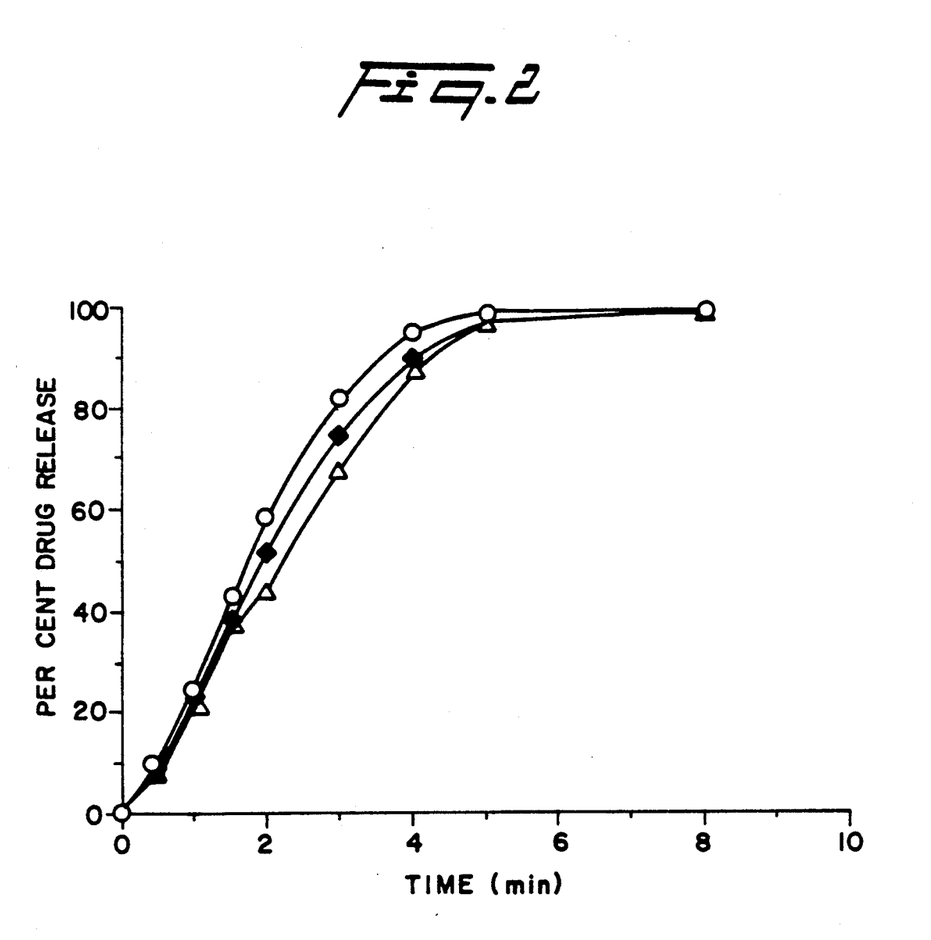
FIG. 2 is a series of plots depicting the dissolution profile of hydrocortisone from tablets containing hydrocortisone-HPβCD complex: Δ, 0% (w/v) CMC; ◆, 0.1% (w/v) CMC; o, 0.25% (w/v) CMC.

The results in FIG. 2 show that hydrocortisone dissolves significantly faster from tablets containing hydrocortisone-HPβCD complex prepared in the presence of CMC than from tablets prepared in the absence of CMC. The results shown in FIG. 2 are the average of four experiments. The dissolution tests were started at time zero. Three minutes later, 68.3% of the hydrocortisone had dissolved from tablets containing hydrocortisone-HPβCD complex formed without the addition of CMC, 74.2% of the hydrocortisone had dissolved from tablets containing hydrocortisone-HPβCD complex formed with the addition of 0.1% (w/v) CMC, and 81.0% of the hydrocortisone had dissolved from tablets containing hydrocortisone-HPβCD complex formed with the addition of 0.25% (w/v) CMC.

EXAMPLE 11

Eye drops containing a carbonic anhydrase inhibitor, acetazolamide, were prepared the following way: Hydroxypropyl methylcellulose (HPMC), 0.25% (w/v), was dissolved in distilled water and hydroxypropyl-β-cyclodextrin MS=0.6, 20% (w/v), benzalkonium chloride [0.02% (w/v)] and the sodium salt of ethylenediaminetetraacetic acid [EDTA, 0.1% (w/v)] were then dissolved in the aqueous HPMC solution. Finally, acetazolamide, 1% (w/v), was added to this solution and dissolved by heating in an autoclave (120° C. for 20 min). The eye drop solution which formed was allowed to equilibrate at room temperature for one week.

Figure 3:
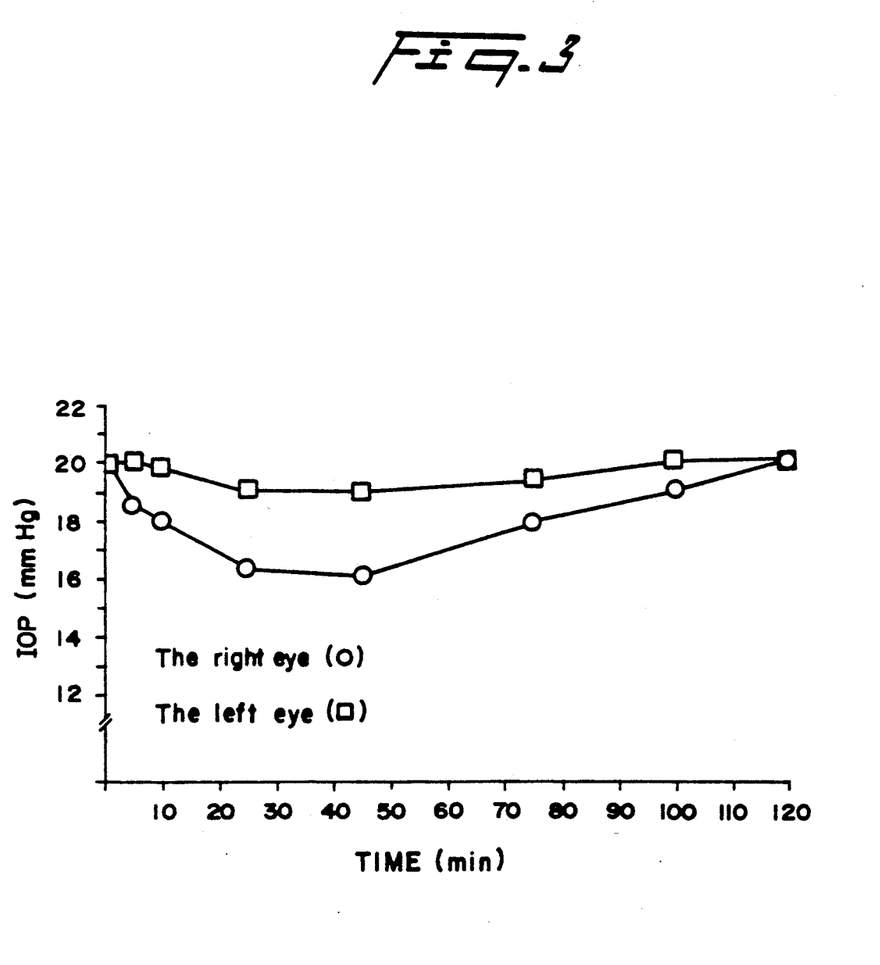
FIG. 3 is a pair of plots illustrating the effect of 1% (w/v) acetazolamide eye drop solution on the intraocular pressure (IOP) of normotensive, conscious, albino rabbits, wherein the right eye received the drug (O) and the left eye was the control (□).

The topical activity of the carbonic anhydrase inhibitor eye drop solution was evaluated in conscious white New Zealand rabbits of either sex (2.5 to 3.5 kg). The intraocular pressure was recorded by a pneumatic tonometer without local anaesthesia. The eye drop solution (0.1 ml) was placed on the cornea of the right eye (the left eye was used as control) and the intraocular pressure was recorded at various time intervals (FIG. 3).

EXAMPLE 12

Hydrocortisone mouthwash was prepared in the following way: HPβCD MS=0.6 (3.5% (w/v)), peppermint oil (0.05% (w/v)), ethanol (12% (v/v)), CMC (0.5% (w/v)), benzalkonium chloride (0.02% (w/v)) and the sodium salt of ethylenediaminetetraacetic acid (0.1% (w/v)) were dissolved in water and the solution was heated in a sealed container in an autoclave (120° C. for 20 minutes). After equilibration to room temperature, hydrocortisone (0.3% (w/v)) was dissolved in the cyclodextrin solution.

The topical activity of the hydrocortisone mouthwash solution was evaluated as follows: Patients were selected on the basis of severe ulceration, causing considerable pain, discomfort, inconvenience with work and the like. Normally the patients had unsuccessfully tried numerous other remedies such as gentian violet, chlorhexidine, silver nitrate, hydrocortisone, and triamcinolone, from a variety of sources. Each patient washed his/her mouth with 5–10 ml of the hydrocortisone mouthwash three to four times a day and the results were evaluated after treatment for two weeks. The results are shown in Table 9.

TABLE 9

Clinical results of treatment of patients with hydrocortisone mouthwash.

| Disease | Number of patients | | | | |
|---|---|---|---|---|---|
| | total | worse | no change | improved | relapsed* |
| Lichen Planus | 17 | 1 | 2 | 14 | 1 |
| Recurrent oral ulceration | 6 | 0 | 0 | 6 | 1 |
| Miscellaneous autoimmune disease | 8 | 0 | 2 | 6 | 1 |

*Relapse, of those which showed improvement, within 6 months after end of treatment.

QUANTITATIVE ANALYSIS

The quantitative determinations of the individual drugs were performed on a reversed-phase high-performance liquid chromatographic (HPLC) component system consisting of a Milton Roy ConstaMetric 3200 solvent delivery system, a Rheodyne 7125 injector, a Spectro Monitor 3200 uv/vis variable wavelength detector and a LiChrosorb®RP-18 5µ (125×4 mm) column. For other conditions, see Table 10. The quantitative determination of econazole was done spectrophotometrically (Perkin-Elmer 550SE uv/vis spectrophotometer) at wavelength 225 nm. Solvent ratios indicated refer to parts by volume.

TABLE 10

Conditions of quantitative drug determination by HPLC.

| Drug | Mobile phase | Flow rate (ml/min) | Wave length (nm) | Retention time (min) |
|---|---|---|---|---|
| Acetazolamide | Acetonitrile, acetic acid, water (10:2:88) containing 0.015% 1-octanesulfonate | 1.5 | 263 | 4.0 |
| Alprazolam | Methanol, water (70:30) | 1.5 | 254 | 2.8 |
| Dexamethasone | Acetonitrile, tetrahydrofuran, water (30:5:65) | 1.5 | 254 | 4.0 |
| Diazepam | Methanol, water (75:25) | 1.5 | 226 | 4.0 |
| Ethoxyzolamide | Acetonitrile, water (35:65) containing 0.1% 1-hexanesulfonate | 1.0 | 254 | 3.2 |
| Hydrocortisone | Acetonitrile, tetrahydrofuran, water (30:1:69) | 1.5 | 254 | 2.6 |
| Miconazole | Methanol, 0.01M aqueous potassium phosphate | 1.5 | 272 | 2.6 |

TABLE 10-continued

Conditions of quantitative drug determination by HPLC.

| Drug | Mobile phase | Flow rate (ml/min) | Wave length (nm) | Retention time (min) |
|---|---|---|---|---|
| | solution (pH = 4.5) (90:10) | | | |
| Oxazepam | Methanol, tetrahydrofuran, water (55:2:43) | 1.5 | 226 | 2.8 |
| Prednisolone | Acetonitrile, acetic acid, water (17:0.5:82.5) | 1.5 | 242 | 4.0 |
| Sulfamethoxazole | Acetonitrile, acetic acid, water (30:1:69) | 1.5 | 253 | 2.4 |
| Temazepam | Methanol, water (70:30) | 1.5 | 275 | 2.8 |
| Triacinolone acetonide | Acetonitrile, water (42:58) | 1.5 | 254 | 2.8 |
| Trimetoprim | Methanol, acetic acid, water (39:1:60) containing 0.005M 1-pentasulfonate | 1.5 | 287 | 2.4 |

EXAMPLE 13

To aqueous solutions containing 20% (w/v) 2-hydroxypropyl-β-cyclodextrin (HPβCD) of molar substitution (MS)=0.6 were added 0.25% (w/v) polyvinylpyrrolidone (PVP), 0.25% (w/v) sodium carboxymethylcellulose (CMC) or 0.25% (w/v) hydroxypropyl methylcellulose (HPMC). The resultant solutions were heated in sealed containers to 120° C. and maintained at that temperature for 30 minutes, then were lyophilized. The solids thus obtained were ground with a mortar and pestle.

The solid cyclodextrin/polymer products were reconstituted with water to afford solutions containing 9.88% (w/v) HPβCD and 0.12% (w/v) PVP, 0.12% (w/v) CMC or 0.12% (w/v) HPMC. The solubilities (S) of three drugs in these solutions and in an aqueous solution containing 10% (w/v) HPβCD without added polymer were then determined as follows:

An excess amount of each drug was added to each of the four cyclodextrin solutions and the solutions were sonicated in an ultrasonic bath for 3 hours, then allowed to equilibrate for 60 hours at room temperature (23° C.). After equilibration, aliquots were filtered through 0.45 mm membrane filters, diluted with a mixture of methanol and water and analyzed by an HPLC method. The results are set forth in Table 11 below, where $S_1$ is the solubility in aqueous solution containing 10% (w/v) HPβCD; $S_2$ is the solubility in aqueous solution containing 9.88% (w/v) HPβCD and 0.12% (w/v) PVP; $S_3$ is the solubility in aqueous solution containing 9.88% (w/v) HPβCD and 0.12% (w/v) CMC; and $S_4$ is the solubility in aqueous solution containing 9.88% (w/v) HPβCD and 0.12% (w/v) HPMC. The results show that a solid polymer/cyclodextrin product can be prepared which has enhanced complexing abilities, and that the drug itself need not be heated to achieve enhancement. Nevertheless, it is expected that a greater increase in solubility would be observed at higher polymer concentrations [e.g. 0.25% (w/v)], and/or if the solutions were heated after addition of the drug. However, by separate preparation of the cyclodextrin/polymer complexing agent as illustrated here, one can readily avoid heating drugs which are unstable at elevated temperature.

TABLE 11

The effect of previously prepared solid HPβCD-polymer complexing agent mixture on the solubility of drugs. Solution $S_1$ contained 10% (w/v) HPβCD. Solutions $S_2$, $S_3$ and $S_4$ contained 9.88% (w/v) HPβCD and 0.12% (w/v) of the polymer.

| Drug | $S_1$ (mg/ml) | $S_2$ (mg/ml) | $S_3$ (mg/ml) | $S_4$ (mg/ml) |
|---|---|---|---|---|
| Carbamazepine | 7.00 | 9.80 | 6.66 | 9.53 |
| Econazole | 4.86 | 5.57 | 5.20 | 6.32 |
| Hydrocortisone | 12.88 | 16.47 | 14.52 | 16.05 |

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A method for enhancing the complexation of cyclodextrin with a lipophilic and/or water-labile drug, said method comprising combining from about 0.1 to about 70% (weight/volume) of cyclodextrin and from about 0.01 to about 5% (weight/volume) of a pharmaceutically acceptable, pharmacologically inactive, water-soluble polymer and a lipophilic and/or water-labile drug in an aqueous medium, the polymer and cyclodextrin being dissolved in the aqueous medium before the drug is added, the aqueous medium which comprises the polymer and cyclodextrin being maintained at from about 30 to about 150° C. for a period of from about 0.1 to about 100 hours before, during and/or after the drug is added, optionally followed by removal of water.

2. The method according to claim 1, wherein the aqueous medium is maintained at from about 30 to about 150° C. for from about 0.1 to about 100 hours before the drug is added.

3. The method according to claim 1, wherein the aqueous medium is maintained at from about 30 to about 150° C. for from about 0.1 to about 100 hours after the drug is added.

4. The method according to claim 1, wherein the cyclodextrin comprises at least one member selected from the group consisting of hydroxypropyl, hydroxyethyl and dihydroxypropyl derivatives of α-, β- and γ-cyclodextrin having a molar degree of substitution of from about 0.05 to about 10.

5. The method according to claim 1, wherein the pharmaceutically acceptable, pharmacologically inactive, water-soluble polymer is a cellulose derivative.

6. The method according to claim 5, wherein the cellulose derivative is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethyl cellulose or sodium carboxymethylcellulose.

7. The method according to claim 6, wherein the cellulose derivative is hydroxypropyl methylcellulose.

8. The method according to claim 6, wherein the cellulose derivative is sodium carboxymethylcellulose.

9. The method according to claim 1, wherein the pharmaceutically acceptable, pharmacologically inactive, water-soluble polymer is a natural polysaccharide or polypeptide.

10. The method according to claim 9, wherein the polysaccharide is inulin, pectin, sodium alginate or agar, or wherein the polypeptide is casein or gelatin.

11. The method according to claim 1, wherein the pharmaceutically acceptable, pharmacologically inactive, water-soluble polymer is a synthetic polymer.

12. The method according to claim 11, wherein the synthetic polymer is a polyvinyl polymer of a copolymer of acrylic acid.

13. The method according to claim 12, wherein the polyvinyl polymer is polyvinyl alcohol, polyvinylpyrrolidone or polystyrene sulfonate.

14. The method according to claim 13, wherein the polyvinyl polymer is polyvinylpyrrolidone.

15. The method according to claim 1, wherein the drug is a carbonic anhydrase inhibitor.

16. The method according to claim 15, wherein the drug is acetazolamide, chlorzolamide, ethoxzolamide or methazolamide.

17. The method according to claim 1, wherein the drug is a β-adrenergic blocking agent.

18. The method according to claim 17, wherein the drug is timolol or atenolol.

19. The method according to claim 1, wherein the drug is a steroid.

20. The method according to claim 19, wherein the steroid is an androgen, estrogen, progestin, diuretic, anabolic agent, anesthetic or glucocorticoid.

21. The method according to claim 20, wherein the drug is hydrocortisone, dexamethasone, prednisolone, 17β-estradiol, 17α-ethinylestradiol, ethinylestradiol 3-methyl ether, estriol, norethindrone, norethindrone acetate, norgestrel, ethisterone, methoxyprogesterone acetate, progesterone, 17-methyltestosterone, triamcinolone, testosterone, spironolactone or alfaxalone.

22. The method according to claim 1, wherein the drug is carbamazepine, phenytoin, ketoconazole, itraconazole, metronidazole benzoate, flubendazole, co-trimoxazole, miconazole, carmustine, chlorambucil, doxorubicin, lomustine, melphalan, methotrexate, dicumarol, nitroglycerin, flunarizine, alprostadil, prostacyclin, digitoxin, digoxin, aspirin, apomorphine, famotidine, furosemide, flurbiprofen, ibuprofen, indomethacin, piroxicam, lidocaine, sulindac, pentobarbital, phenobarbital, secobarbital, chlordiazepoxide, diazepam, medazepam, oxazepam or lorazepam.

23. The method according to claim 1, wherein the drug is the reduced, biooxidizable, blood-brain barrier penetrating, lipoidal dihydropyridine form of a dihydropyridine⇌pyridinium salt redox system for brain-targeted drug delivery.

24. The method according to claim 23, wherein the dihydropyridine form is a compound of the formula

[D-DHC]

wherein [D] is a centrally acting drug species and [DHC] is the reduced, biooxidizable, blood-brain barrier penetrating, lipoidal form of a dihydropyridine⇌pyridinium salt redox carrier.

25. The method according to claim 24, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

26. The method according to claim 1, wherein the cyclodextrin is hydroxypropyl-β-cyclodextrin or hydroxypropyl-γ-cyclodextrin, the polymer is hydroxypropyl methylcellulose, sodium carboxymethylcellulose or polyvinylpyrrolidone and the drug is a carbonic anhydrase inhibitor or a steroid.

27. A method for solubilizing and/or stabilizing a lipophilic and/or water-labile drug in an aqueous medium, said method comprising complexing said drug in an aqueous medium comprising from about 0.1 to about 70% (weight/volume) of cyclodextrin and from about 0.01 to about 5% (weight/volume) of a pharmaceutically acceptable, pharmacologically inactive, water-soluble polymer, the polymer and cyclodextrin being dissolved in the aqueous medium before the drug is added, the aqueous medium which comprises the polymer and cyclodextrin being maintained at from about 30° to about 150° C. for a period of from about 0.1 to about 100 hours before, during and/or after the drug is added.

28. The method according to claim 27, wherein the aqueous medium is maintained at from about 30° to about 150° C. for from about 0.1 to about 100 hours before the drug is added.

29. The method according to claim 27, wherein the aqueous medium is maintained at from about 30° to about 150° C. for from about 0.1 to about 100 hours after the drug is added.

30. The method according to claim 27, wherein the cyclodextrin comprises at least one member selected from the group consisting of hydroxypropyl, hydroxyethyl and dihydroxypropyl derivatives of α-, β- and γ-cyclodextrin having a molar degree of substitution of from about 0.05 to about 10.

31. The method according to claim 27, wherein the pharmaceutically acceptable, pharmaceutically inactive, water-soluble polymer is a cellulose derivative.

32. The method according to claim 31, wherein the cellulose derivative is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethylcellulose or sodium carboxymethylcellulose.

33. The method according to claim 32, wherein the cellulose derivative is hydroxypropyl methylcellulose.

34. The method according to claim 32, wherein the cellulose derivative is sodium carboxymethylcellulose.

35. The method according to claim 27, wherein the pharmaceutically acceptable, pharmacologically inactive, water-soluble polymer is a natural polysaccharide or polypeptide.

36. The method according to claim 35, wherein the polysaccharide is inulin, pectin, sodium alginate or agar, or wherein the polypeptide is casein or gelatin.

37. The method according to claim 27, wherein the pharmaceutically acceptable, pharmacologically inactive, water-soluble polymer is a synthetic polymer.

38. The method according to claim 37, wherein the synthetic polymer is a polyvinyl polymer or a copolymer of acrylic acid.

39. The method according to claim 38, wherein the polyvinyl polymer is polyvinyl alcohol, polyvinylpyrrolidone or polystyrene sulfonate.

40. The method according to claim 39, wherein the polyvinyl polymer is polyvinylpyrrolidone.

41. The method according to claim 27, wherein the drug is a carbonic anhydrase inhibitor.

42. The method according to claim 41, wherein the drug is acetazolamide, chlorzolamide, ethoxzolamide or methazolamide.

43. The method according to claim 27, wherein the drug is a β-adrenergic blocking agent.

44. The method according to claim 43, wherein the drug is timolol or atenolol.

45. The method according to claim 27, wherein the drug is a steroid.

46. The method according to claim 45, wherein the steroid is an androgen, estrogen, progestin, diuretic, anabolic agent, anesthetic or glucocorticoid.

47. The method according to claim 46, wherein the drug is hydrocortisone, dexamethasone, prednisolone, 17β-estradiol, 17α-ethinylestradiol, ethinylestradiol 3-methyl ether, estriol, norethindrone, norethindrone acetate, norgestrel, ethisterone, methoxyprogesterone acetate, progesterone, 17-methyltestosterone, triamcinolone, testosterone, spironolactone or alfaxalone.

48. The method according to claim 27, wherein the drug is carbamazepine, phenytoin, ketoconazole, itraconazole, metronidazole benzoate, flubendazole, co-trimoxazole, miconazole, carmustine, chlorambucil, doxorubicin, lomustine, melphalan, methotrexate, dicumarol, nitroglycerin, flunarizine, alprostadil, prostacyclin, digitoxin, digoxin, aspirin, apomorphine, famotidine, furosemide, flurbiprofen, ibuprofen, indomethacin, piroxicam, lidocaine, sulindac, pentobarbital, phenobarbital, secobarbital, chlordiazepoxide, diazepam, medazepam, oxazepam, or lorazepam.

49. The method according to claim 27, wherein the drug is the reduced, biooxidizable, blood-brain barrier penetrating, lipoidal dihydropyridine form of a dihydropyridine⇌pyridinium salt redox system for brain-targeted drug delivery.

50. The method according to claim 49, wherein the dihydropyridine form is a compound of the formula

[D-DHC]

wherein [D] is a centrally acting drug species and [DHC] is the reduced, biooxidizable, blood-brain barrier penetrating, lipoidal form of a dihydropyridine⇌pyridinium salt redox carrier.

51. The method according to claim 50, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

52. The method according to claim 27, wherein the cyclodextrin is hydroxypropyl-β-cyclodextrin or hydroxypropyl-γ-cyclodextrin, the polymer is hydroxypropyl methylcellulose, sodium carboxymethylcellulose or polyvinylpyrrolidone and the drug is a carbonic anhydrase inhibitor or a steroid.

* * * * *